United States Patent
Edic et al.

(10) Patent No.: US 7,382,852 B2
(45) Date of Patent: *Jun. 3, 2008

(54) METHOD AND APPARATUS FOR CORRECTING MOTION IN IMAGE RECONSTRUCTION

(75) Inventors: Peter Michael Edic, Albany, NY (US); Maria Iatrou, Clifton Park, NY (US); Erdogan Cesmeli, Brookfield, WI (US); Bruno De Man, Clifton Park, NY (US); Samit Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/804,861

(22) Filed: May 21, 2007

(65) Prior Publication Data

US 2007/0217568 A1    Sep. 20, 2007

Related U.S. Application Data

(63) Continuation of application No. 10/625,361, filed on Jul. 23, 2003, now Pat. No. 7,221,728.

(60) Provisional application No. 60/398,463, filed on Jul. 25, 2002, provisional application No. 60/397,658, filed on Jul. 23, 2002.

(51) Int. Cl.
    *G01N 23/00* (2006.01)

(52) U.S. Cl. .............................. 378/8; 378/4

(58) Field of Classification Search ................. 378/4, 378/8, 15, 16, 20
See application file for complete search history.

(56) References Cited

U.S. PATENT DOCUMENTS

| | | | |
|---|---|---|---|
| 2,340,500 | A | 11/1944 | Zunick et al. |
| 4,057,725 | A | 11/1977 | Wagner |
| 4,182,311 | A | 1/1980 | Seppi et al. |
| 4,196,352 | A | 4/1980 | Beringer et al. |
| 4,274,005 | A | 6/1981 | Yamamura et al. |
| 4,284,896 | A | 8/1981 | Stonestrom |
| 4,384,359 | A | 5/1983 | Franke |
| 4,547,892 | A | 10/1985 | Richey et al. |
| 4,947,412 | A | 8/1990 | Mattson |
| 4,965,726 | A | 10/1990 | Heuscher et al. |
| 4,991,190 | A | 2/1991 | Mori |
| 5,166,961 | A | 11/1992 | Brunnett |
| 5,175,754 | A | 12/1992 | Casey et al. |
| 5,228,070 | A | 7/1993 | Mattson |

(Continued)

OTHER PUBLICATIONS

Lalush, David C., Feasibility of Transmission Micro-CT with Two Fan Beam Sources, IEEE, pp. 1283-1286, Sep. 1-5, 2004, vol. 4, San Francisco, California.

*Primary Examiner*—Hoon Song
(74) *Attorney, Agent, or Firm*—Fletcher Yoder

(57) ABSTRACT

One or more techniques are provided for adapting a reconstruction process to account for the motion of an imaged object or organ, such as the heart. In particular, projection data of the moving object or organ is acquired using a slowly rotating CT gantry. Motion data may be determined from the projection data or from images reconstructed from the projection data. The motion data may be used to reconstruct motion-corrected images from the projection data. The motion-corrected images may be associated to form motion-corrected volume renderings.

16 Claims, 10 Drawing Sheets

U.S. PATENT DOCUMENTS

| | | | |
|---|---|---|---|
| 5,259,012 A | 11/1993 | Baker et al. |
| 5,262,946 A | 11/1993 | Heuscher |
| 5,276,614 A | 1/1994 | Heuscher |
| 5,305,363 A | 4/1994 | Burke et al. |
| 5,377,249 A | 12/1994 | Wiesent et al. |
| 5,383,231 A | 1/1995 | Yamagishi |
| 5,396,418 A | 3/1995 | Heuscher |
| 5,412,562 A | 5/1995 | Nambu et al. |
| 5,438,605 A | 8/1995 | Burke et al. |
| 5,485,493 A | 1/1996 | Heuscher et al. |
| 5,491,734 A | 2/1996 | Boyd et al. |
| 5,544,212 A | 8/1996 | Heuscher |
| 5,570,403 A | 10/1996 | Yamazaki et al. |
| 5,633,906 A | 5/1997 | Hell et al. |
| 5,654,995 A | 8/1997 | Flohr |
| 5,719,914 A | 2/1998 | Rand et al. |
| 5,764,721 A | 6/1998 | Light et al. |
| 5,848,117 A | 12/1998 | Urchuk et al. |
| 5,966,422 A | 10/1999 | Dafni et al. |
| 6,002,738 A | 12/1999 | Cabral et al. |
| 6,047,040 A | 4/2000 | Hu et al. |
| 6,125,167 A | 9/2000 | Morgan |
| 6,130,929 A | 10/2000 | Saha |
| 6,183,139 B1 | 2/2001 | Solomon et al. |
| 6,208,711 B1 | 3/2001 | Rand et al. |
| 6,229,870 B1 | 5/2001 | Morgan |
| 6,236,705 B1 | 5/2001 | Stergiopoulos et al. |
| 6,236,709 B1 | 5/2001 | Perry et al. |
| 6,252,924 B1 | 6/2001 | Davantes et al. |
| 6,272,200 B1 | 8/2001 | Pan et al. |
| 6,333,968 B1 | 12/2001 | Whitlock et al. |
| 6,353,653 B1 | 3/2002 | Edic |
| 6,385,282 B1 | 5/2002 | Francke et al. |
| 6,421,412 B1 | 7/2002 | Hsieh et al. |
| 6,453,003 B1 | 9/2002 | Springer et al. |
| 6,459,755 B1 | 10/2002 | Li |
| 6,466,640 B1 | 10/2002 | Taguchi |
| 6,507,639 B1 | 1/2003 | Popescu |
| 6,522,712 B1 | 2/2003 | Yavuz et al. |
| 6,535,570 B2 | 3/2003 | Stergiopoulos et al. |
| 6,674,837 B1 | 1/2004 | Taskar et al. |
| 6,731,716 B2 | 5/2004 | Mihara et al. |
| 6,754,300 B2 | 6/2004 | Hsieh et al. |
| 6,760,399 B2 | 7/2004 | Malamud |
| 6,795,521 B2 | 9/2004 | Hsu et al. |
| 6,807,248 B2 | 10/2004 | Mihara et al. |
| 6,876,724 B2 | 4/2005 | Zhou et al. |
| 6,885,004 B2 | 4/2005 | Taskar et al. |
| 6,914,959 B2 | 7/2005 | Bailey et al. |
| 6,920,196 B2 | 7/2005 | Ueno et al. |
| 6,934,357 B2 | 8/2005 | Boyd et al. |
| 7,072,436 B2 | 7/2006 | Pelc |
| 7,145,981 B2 | 12/2006 | Pelc |
| 7,221,728 B2 * | 5/2007 | Edic et al. ............ 378/8 |
| 2002/0085674 A1 | 7/2002 | Price et al. |
| 2004/0014710 A1 | 6/2004 | Ozaki |
| 2004/0136490 A1 | 7/2004 | Edic et al. |
| 2004/0213378 A1 | 10/2004 | Zhou et al. |
| 2005/0135550 A1 | 6/2005 | De Man et al. |
| 2005/0175143 A1 | 8/2005 | Miyazaki et al. |

* cited by examiner

METHOD AND APPARATUS FOR CORRECTING MOTION IN IMAGE RECONSTRUCTION

CROSS-REFERENCE TO RELATED APPLICATIONS

This application is a continuation of Ser. No. 10/625,361, filed Jul. 23, 2003 now U.S. Pat. No. 7,221,728, entitled METHOD AND APPARATUS FOR CORRECTING MOTION IN IMAGE RECONSTRUCTION in the name of Peter Michael Edic et al., incorporated by reference herein in its entirety, which claims the benefit of U.S. Provisional Application No. 60/397,658 filed on Jul. 23, 2002 and U.S. Provisional Application 60/398,463 filed on Jul. 25, 2002.

BACKGROUND OF THE INVENTION

The present invention relates generally to the field of medical imaging and more specifically to the field of imaging dynamic, internal tissue, such as cardiac tissue, by computed tomography. In particular, the present invention relates to the characterization of internal motion and to the reconstruction of images that account for the characterized motion.

Computed tomography (CT) imaging systems measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced projection images. A CT system processes X-ray transmission data to generate 2D maps of the line integral of linear attenuation coefficients of the scanned object at multiple view angle positions. These data are then reconstructed to produce images, which are typically displayed on a monitor, and may be printed or reproduced on film. A virtual 3-D image may also be produced by a CT examination.

CT scanners operate by projecting fan shaped or cone shaped X-ray beams from an X-ray source. The X-ray beams may be collimated to control the shape and spread of the beams. The X-ray beams are attenuated as they pass through the object to be imaged, such as a patient. The attenuated beams are detected by a set of detector elements. Each detector element produces a signal affected by the attenuation of the X-ray beams, and the data are processed to produce signals that represent the line integrals of the attenuation coefficients of the object along the X-ray paths. These signals are typically called "projection data" or just "projections". By using reconstruction techniques, such as filtered backprojection, useful images may be formulated from a collection of projections. The images may in turn be associated to form a volume, allowing generation of a volumetric rendering of a region of interest. The locations of objects, such as pathologies or other anatomical structures, may then be identified either automatically, such as by a computer-assisted detection (CAD) algorithm or, more conventionally, such as by a trained radiologist. CT scanning provides certain advantages over other types of techniques in diagnosing disease, particularly because it illustrates the accurate anatomical information about the body. Further, CT scans may help physicians distinguish between types of abnormalities more accurately.

CT imaging techniques, however, may present certain challenges when imaging dynamic internal tissues, such as the heart. For example, in cardiac imaging, the motion of the heart causes inconsistencies in the projection data, which, after reconstruction, may result in various motion-related image artifacts such as blurring, streaking, or discontinuities. To reduce the occurrence of motion-related image artifacts, various techniques may be employed to improve the temporal resolution of the imaging system, thereby reducing the effects of the moving tissue. Temporal resolution may generally be improved by decreasing the rotation time of the CT gantry. In this way, the amount of motion that occurs within the temporal window associated with the acquisition of a projection data set is minimized.

Temporal resolution may be further improved by the choice of reconstruction algorithm. For example, segment reconstruction algorithms, such as half-scan reconstruction algorithms, may be employed in the reconstruction process. The segment reconstruction algorithms typically reconstruct images using projection data collected over an angular displacement of the gantry equaling 180° plus the fan angle ($\alpha$) of the X-ray beam. Because the acquisition of projection data during rotation of the gantry by 180°+$\alpha$ is more rapid than acquisition during 360° of gantry rotation to acquire the requisite projection data, the temporal resolution of the reconstruction process is improved.

Multi-sector reconstruction techniques may also improve the temporal resolution of the reconstructed images by using projection data acquired during multiple rotations of the gantry using a multi-slice detector array. The projection data set used for reconstruction is composed of two or more sectors of projection data that are acquired from different cardiac cycles on multiple rotations of the gantry. The sectors comprise the projection data acquired during a short span of the gantry rotation, typically less than half of a rotation. The sectors, therefore, have good temporal resolution if acquired by a rapidly rotating gantry, thereby providing a good effective temporal resolution for the aggregate projection data set used in reconstruction.

Using the techniques discussed above, third and fourth generation CT systems existing today are capable of temporal resolutions of approximately 300 ms for segment reconstruction strategies. However, a temporal resolution of approximately 20 ms is desirable in order to "freeze" cardiac motion, thereby minimizing motion related artifacts in the reconstructed images. Presently, improving temporal resolution by the above techniques has typically focused on further increasing the rotational speed of the gantry.

However, as the rotational speed of the gantry increases, the centripetal force on the gantry components also increases. The increasing centripetal force and the tolerances of the gantry components may comprise, therefore, a mechanical limitation to increases in gantry velocity. Furthermore, to obtain consistent image quality in terms of signal-to-noise ratio, a constant X-ray flux should be delivered to the imaged object or patient during the scan interval. Achieving a constant X-ray flux, however, places increased demand on the X-ray tube, particularly in regard to tube output, and on the components that are required to cool the X-ray tube. Both mechanical and X-ray flux considerations, therefore, are obstacles to increasing the gantry rotation speed sufficiently to achieve a temporal resolution of 20 ms or better in CT reconstructions. A technique for achieving a temporal resolution without increasing gantry rotation speed is therefore desirable.

BRIEF DESCRIPTION OF THE INVENTION

The present technique provides a novel method and apparatus for improving temporal resolution of a CT imaging system. The technique employs a slowly rotating CT gantry that acquires projection data of an object or patient. Motion within the object, such as cardiac motion within a patient, is identified and used to warp the reconstruction grid at any instant in time and at any given view angle of the gantry. The measured projection data may then be reconstructed, such as by filtered backprojection, on the warped reconstruction grid to generate a motion corrected image. Motion corrected images for the entire region of interest may be created in this manner and associated for viewing, such as by a radiologist or physician.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
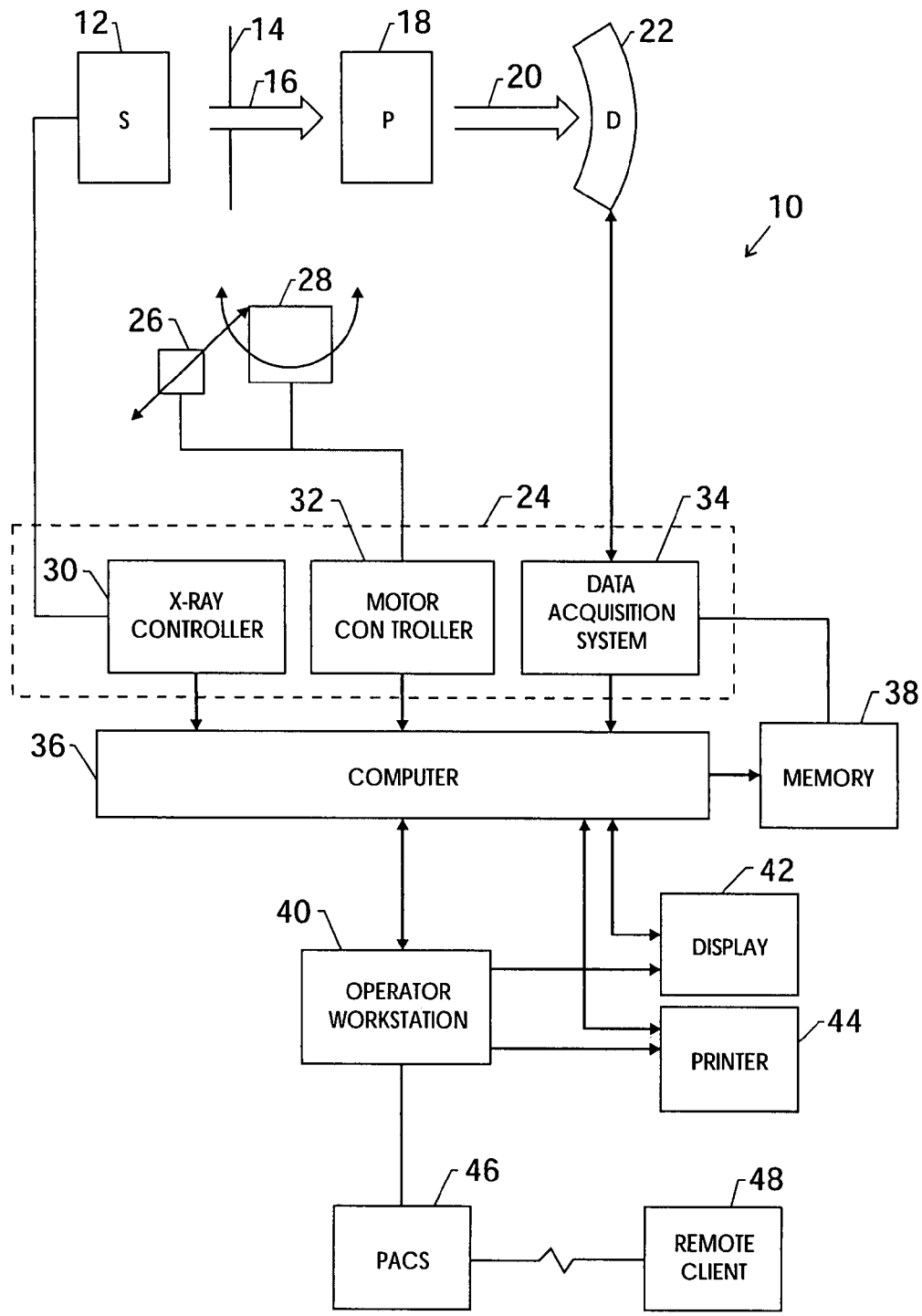
FIG. 1 is a diagrammatical view of an exemplary imaging system in the form of a CT imaging system for use in producing processed images, in accordance with one aspect of the present technique.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. The stream of radiation 16 may be generally fan or cone shaped, depending on the configuration of the detector array, discussed below, as well as the desired method of data acquisition. A portion of the radiation 20 passes through or around the subject and impacts a detector array, represented generally as reference numeral 22. Detector elements of the array produce electrical signals that represent the intensity of the incident X-ray beam. The signals generated by the detector array 22 may be subsequently processed to reconstruct an image of the features within the subject.

A variety of configurations of the detector 22 may be employed in conjunction with the techniques described herein. For example, the detector 22 may be a multi-row detector, such as a detector 22 comprising eight or sixteen rows of detector elements, that achieves limited longitudinal coverage of the object or patient being scanned. Similarly, the detector 22 may be an area detector, such as a detector 22 comprising hundreds of rows of detector elements, that allow positioning of the entire object or organ being imaged within the field of view of the system 10 at each angular position of the gantry, enabling measurement of the two-dimensional projection data required for image reconstruction of the whole organ. Other detector 22 configurations may also be suitable. For example, the detector array 22 may comprise a central, high-resolution portion with or without a lower-resolution portion extending from two or more sides of the central portion. If present, the lower resolution extension may expand the field of view of the system 10 to encompass the entire object being imaged. In general, it is desirable to center the object or organ to be imaged, particularly a dynamic organ such as the heart, within the field of view defined by the detector array 22.

The source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18. Although the depicted system 10 is a third generation CT scanner, the methods to generate signals representative of cardiac motion described herein apply to all advanced generation CT systems.

Additionally, as will be appreciated by those skilled in the art, the source of radiation may be controlled by an X-ray controller 30 disposed within the system controller 24.

Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image. Additionally, the reconstructed image may also be printed by a printer 44, which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
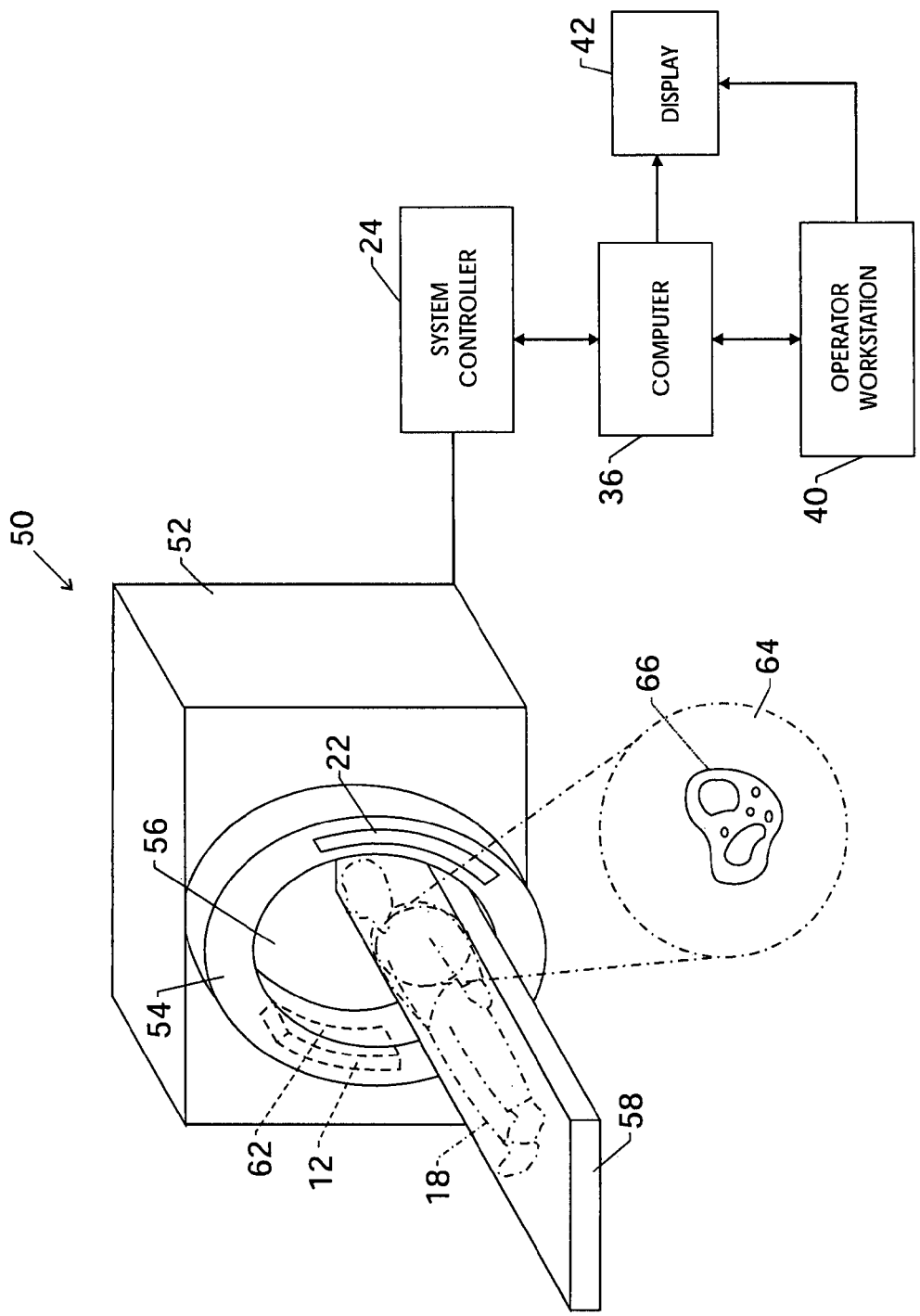
FIG. 2 is another diagrammatical view of a physical implementation of the CT system of FIG. 1, in accordance with one aspect of the present technique.

Referring generally to FIG. 2, an exemplary imaging system utilized in a present embodiment may be a CT scanning system 50. The CT scanning system 50 may be a multi-slice detector CT (MDCT) system that offers selection of axial coverage, while providing high gantry rotational speed and high spatial resolution. Alternately, the CT scanning system 50 may be a volumetric CT (VCT) system utilizing a cone-beam geometry and an area detector to allow the imaging of a volume, such as an entire internal organ of a patient. Furthermore, as noted above, the CT scanning system 50 may be a third generation CT imaging system, as depicted, or may be an advanced generation CT imaging system.

The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, typically via linear displacement of the table 58 by the linear positioning subsystem 26 (see FIG. 1). The gantry 54 is illustrated with the source of radiation 12, typically an X-ray tube that emits X-ray radiation from a focal point 62. For cardiac imaging, the stream of radiation is directed towards a cross section of the patient 18 including the heart.

In typical operation, X-ray source 12 projects an X-ray beam from the focal point 62 toward the detector array 22. The collimator 14 (see FIG. 1), such as lead or tungsten shutters, typically defines the size and shape of the X-ray beam that emerges from the X-ray source 12. The detector 22 is generally formed by a plurality of detector elements, which detect the X-rays that pass through and around a subject of interest, such as the heart or chest. Each detector element produces an electrical signal that represents the intensity of the X-ray beam at the position of the element during the time the beam strikes the detector. The gantry 54 is rotated around the subject of interest so that a plurality of radiographic views may be collected by the computer 36.

Thus, as the X-ray source 12 and the detector 22 rotate, the detector 22 collects data of the attenuated X-ray beams. Data collected from the detector 22 then undergoes preprocessing and calibration to condition the data to represent the line integrals of the attenuation coefficients of the scanned objects. The processed data, commonly called projections, may then be filtered and backprojected to formulate an image of the scanned area. A formulated image may incorporate, in certain modes, projection data acquired from less or more than 360 degrees of gantry rotation.

Once reconstructed, the cardiac image produced by the system of FIGS. 1 and 2 reveals the heart of the patient 18. As illustrated generally in FIG. 2, the image 64 may be displayed to show patient features, such as indicated at reference numeral 66 in FIG. 2. In traditional approaches to diagnosis of medical conditions, such as disease states, and more generally of medical conditions or events, a radiologist or physician would consider the reconstructed image 64 to discern characteristic features of interest. Such features 66 include coronary arteries or stenotic lesions of interest, and other features, which would be discernable in the image, based upon the skill and knowledge of the individual practitioner. Other analyses may be based upon capabilities of various CAD algorithms.

Reconstruction of Motion-Corrected Images

As will be appreciated by those skilled in the art, reconstruction of an image 64 may be complicated by a variety of factors. For example, reconstructed images 64 of dynamic tissue may include motion-related image artifacts that are attributable to the movement of the tissue during imaging. To reduce motion-related artifacts, it is generally desirable to improve the temporal resolution of the CT reconstruction process.

Figure 3:
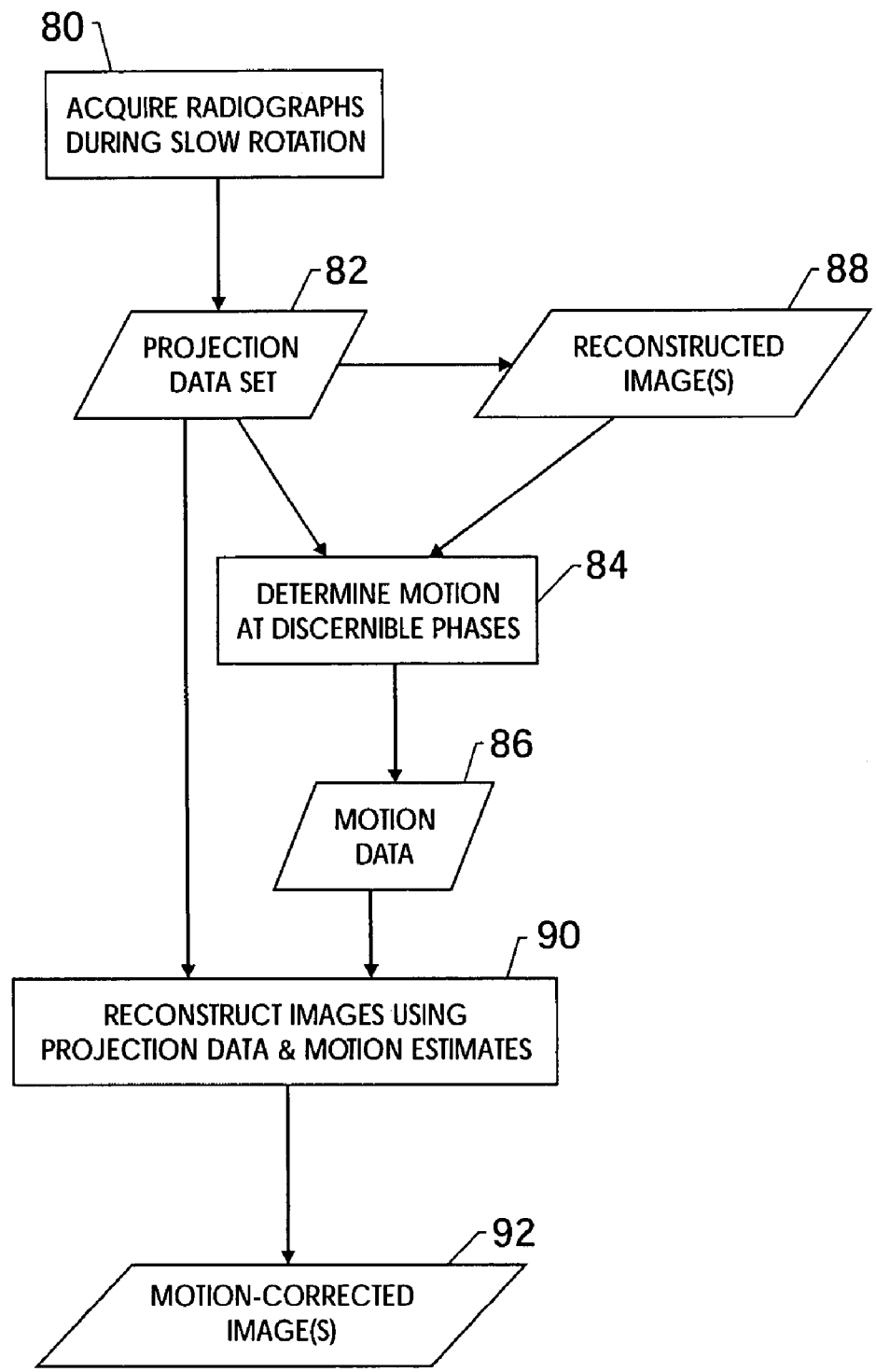
FIG. 3 is a flowchart depicting a technique for generating motion-corrected images of a moving object, in accordance with one aspect of the present technique.

For example, referring to FIG. 3, a process for improving the effective temporal resolution of a CT reconstruction process is depicted. As depicted as step 80, radiographs of the object within the field of view are acquired by a slowly rotating gantry 54, such as a gantry rotation that takes 10 or more seconds to complete. In one aspect of the present technique the gantry 54 completes a rotation in approximately fifteen seconds. The radiographs may be acquired in a single rotation of the gantry 54 or over the course of more than one such rotation. Alternatively, the radiographs may be acquired over the course of a partial rotation, i.e., less than 360° of rotation, depending on the reconstruction methodology to be employed. If the object being imaged undergoes repetitive or cyclic motion, more than one cycle of motion may be completed during the rotation or rotations of the gantry 54. For example, if the object being imaged is a heart, more than one cardiac cycle will typically be completed during a single rotation of the gantry 54. For simplicity, a single rotation of the slowly rotating gantry 54 will be assumed, though one skilled in the art will readily understand that the techniques described may be easily adapted to process projection data 82 collected by multiple slow rotations of the gantry 54 for additional locations on the object being imaged.

The acquired radiographs may be processed to form a projection data set 82. The motion of the imaged object may be determined at discernible phases, as depicted at step 84, to form a set of motion data 86. The motion at a phase of movement may be determined from the projection data set 82 and/or from one or more images 88 reconstructed from the projection data set 82. The determination of motion data 86 may be facilitated by identifying specific phases of motion of the object being imaged using the projection data 82 themselves or from an external indicator of the phase information of the imaged object, for instance with a measured electro-cardiogram (ECG) signal if the object is the heart. Once determined, the motion data 86 may be used to correct for the motion of the object during imaging when reconstructing the projection data set 82, as depicted at step 90. One or more motion-corrected images 92 may be generated by the motion-corrected reconstruction process.

Figure 4:
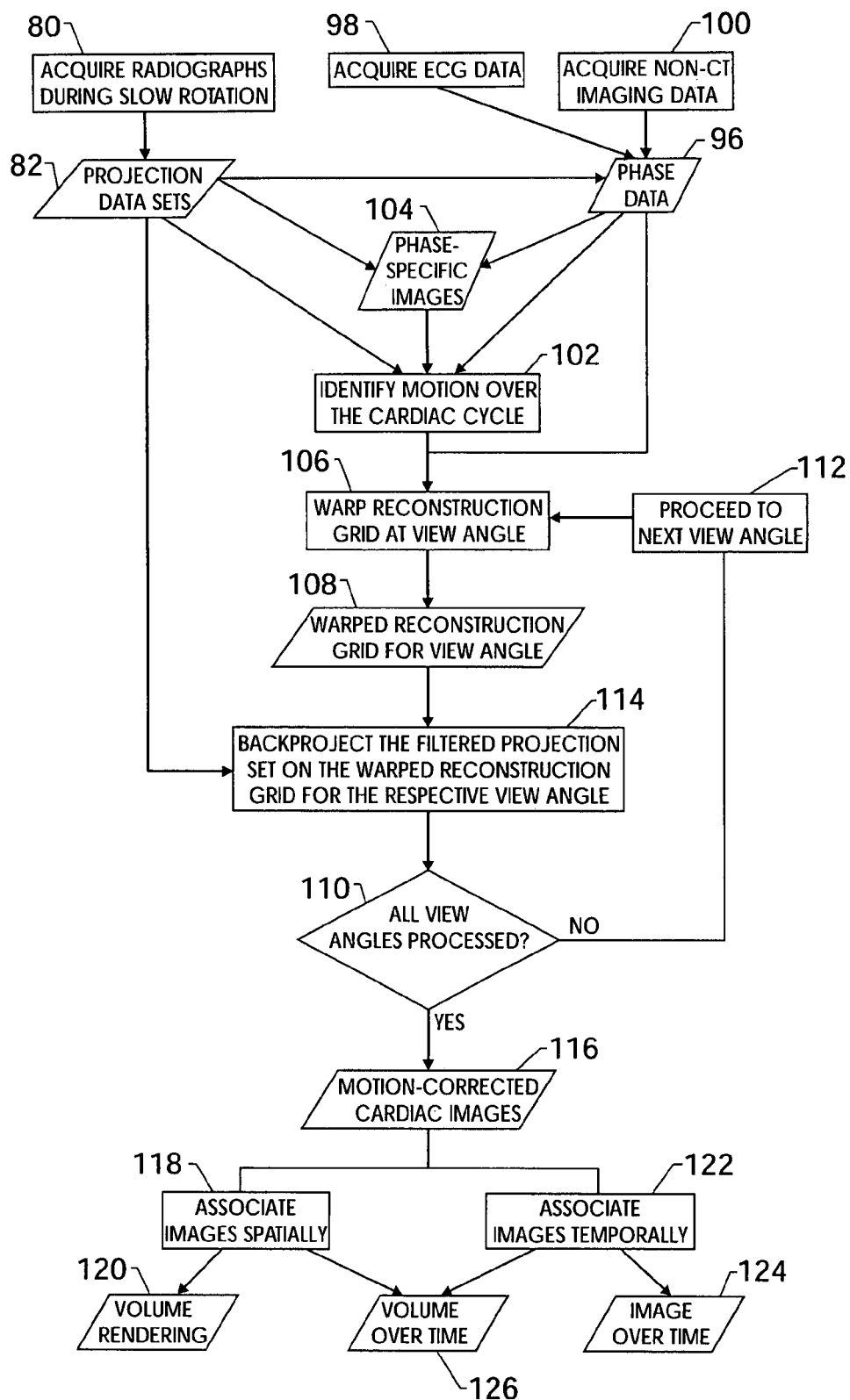
FIG. 4 is a flowchart depicting the technique for generating motion-corrected cardiac images using an exemplary CT system, in accordance with one aspect of the present technique.

Application of the general technique depicted in FIG. 3 to cardiac imaging using a CT scanning system 50 is depicted in FIG. 4. A projection data set 82 is a collection of processed radiographs acquired by a slowly rotating CT gantry 54, as depicted at step 80. The projection data 82 may contain data inconsistencies attributable to cardiac motion during the data acquisition step 80.

In addition, phase data 96 of the cardiac cycle may be acquired or generated. The phase data 96 may be derived from the projection data 82, from an ECG signal acquired concurrent with the radiographs, as depicted at step 98, or from imaging data acquired via other imaging modalities, as depicted at step 100. The phase data 96 may facilitate the identification of the motion of the heart at a phase of the cardiac cycle, as depicted at step 102. For example, the phase data 96 may facilitate the estimation of motion during a specific phase of the cardiac cycle from either the projection data 82 or from phase-specific images 104 reconstructed from the projection data 82, such as may be generated via retrospective gating of the projection data 82 using the phase data 96. Once the motion during the entire cardiac cycle is identified, the reconstruction grid at a specified view angle associated with a set of projection data may be warped or adapted to account for the motion of the heart at that phase of the cardiac cycle, thereby using the phase data 96, as depicted at step 106. The resulting warped reconstruction grid 108 mitigates the inconsistencies in the projection data 82 attributable to the cardiac motion at the particular view angle. If additional projection data are to be filtered and backprojected, as determined at decision block 110, the motion identification, the usage of the phase data 96, and the subsequent acts may be repeated for the remaining view angles of interest, as depicted at step 112.

After a warped reconstruction grid 108 has been generated, the projection data set 82 may then be filtered and backprojected onto the respective warped reconstruction grid 108 for each view angle position. After projection data 82 from all gantry view angles have been filtered and back-projected on appropriate warped reconstruction grids 108 relative to phase data 96, motion-corrected cardiac images 116 are generated, as depicted at step 114. As one skilled in the art will understand, the order of these steps may vary. For example, the motion-corrected cardiac images 116 may be reconstructed as each respective warped reconstruction grid 108 is generated, as depicted in FIG. 4. Alternately, reconstruction of the motion-corrected images 116 may occur after the generation of all the warped reconstruction grids 108 of interest as a separate and/or discrete process. Such variations in the execution of the process are considered to be well within the scope of the technique.

Once the desired motion-corrected cardiac images 116 have been reconstructed, the images may be associated spatially and/or temporally. For example, spatially proximate or adjacent images may be associated spatially, as depicted at step 118, to generate a static volume rendering 120 at a point in time during the cardiac cycle or at a desired phase. Similarly, temporally proximate or adjacent images 116 may be associated temporally, as depicted at step 122, to generate an image sequence or video 124 depicting a slice or cross-section over time, i.e., over the course of the cardiac cycle. Similarly, the motion-corrected cardiac images 116 may be associated both spatially and temporally to generate a dynamic volume rendering 126 depicting the motion of the volume over time.

Determination of Motion

As will be readily apprehended by those skilled in the art, the motion of the heart may be determined in various ways that may be used in conjunction with the process for generating motion-corrected cardiac images 116 described above. For example, motion may be identified using only the projection data 82. In particular, because the projection data 82 varies only slightly from view to view, the motion information may be determined at step 102 by identifying the warping of the image space to account for the inconsistencies observed in the projection data 82.

Image data acquired, either concurrently or sequentially, by other imaging modalities, such as cardiac ultrasound or tagged MRI, may be used to determine the cardiac motion directly at step 102. Alternately, image data from other modalities, ECG data, or data derived from the projections 82 themselves, such as via techniques employing consistency conditions to analyze the projection data 82 and/or to compare the moments of the projection data 82, may be used to determine phase data 96, i.e., the timing associated with the respective cardiac phases during the acquisition of the projection data 82. The phase data 96 may be used to retrospectively gate, i.e., select, the projection data 82 that corresponds in phase. The gated projection data may be reconstructed to generate images of the heart at the various phases of the cardiac cycle. The phase-specific images may then be used to determine the motion of the heart from phase to phase at step 102. While these generalized techniques are acceptable for providing motion information that may be used to form a warped reconstruction grid 108, other techniques also exist for determining the cardiac motion at step 102.

A. Iterative Reconstruction using Weighted Views

Figure 5:
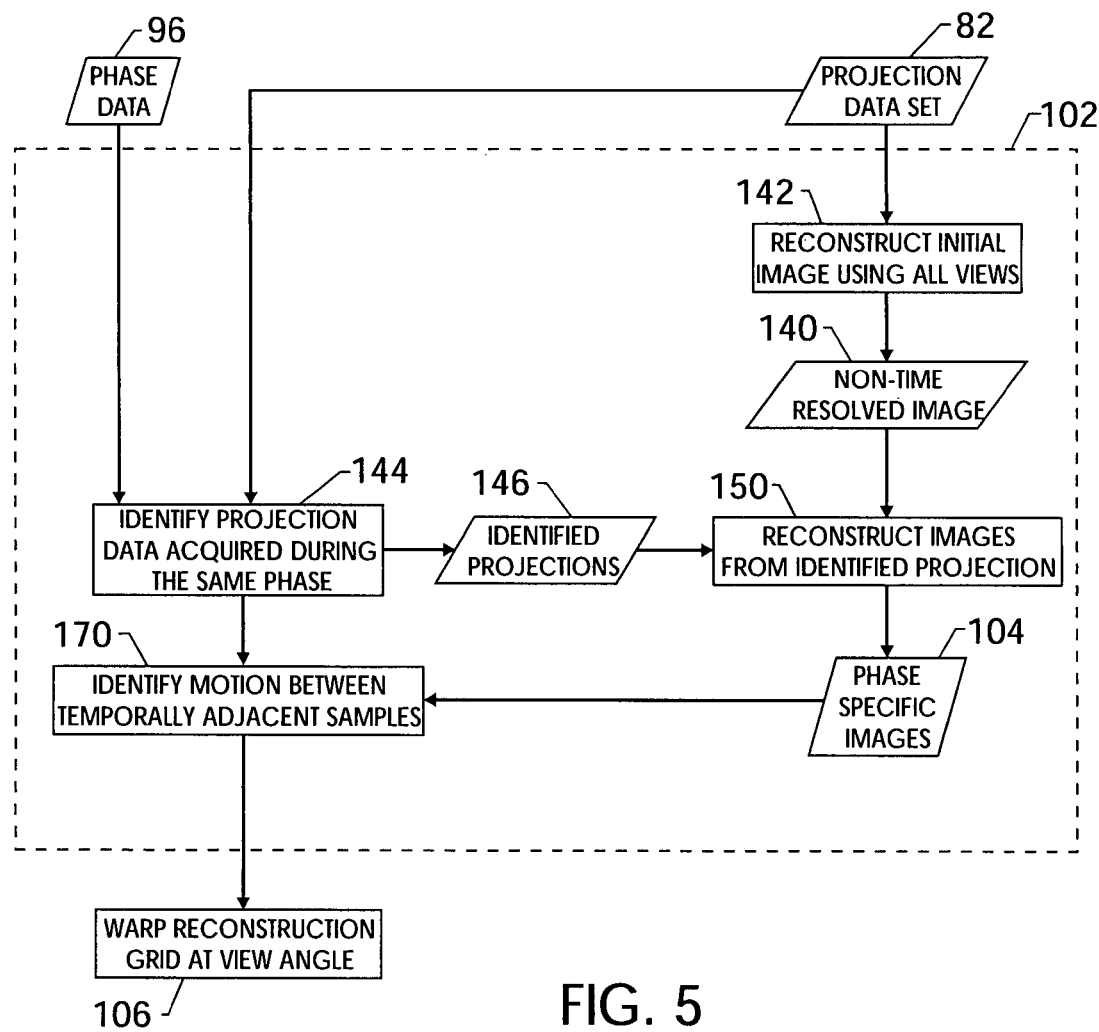
FIG. 5 is a flowchart depicting a technique for determining cardiac motion, in accordance with one aspect of the present technique.
Figure 6:
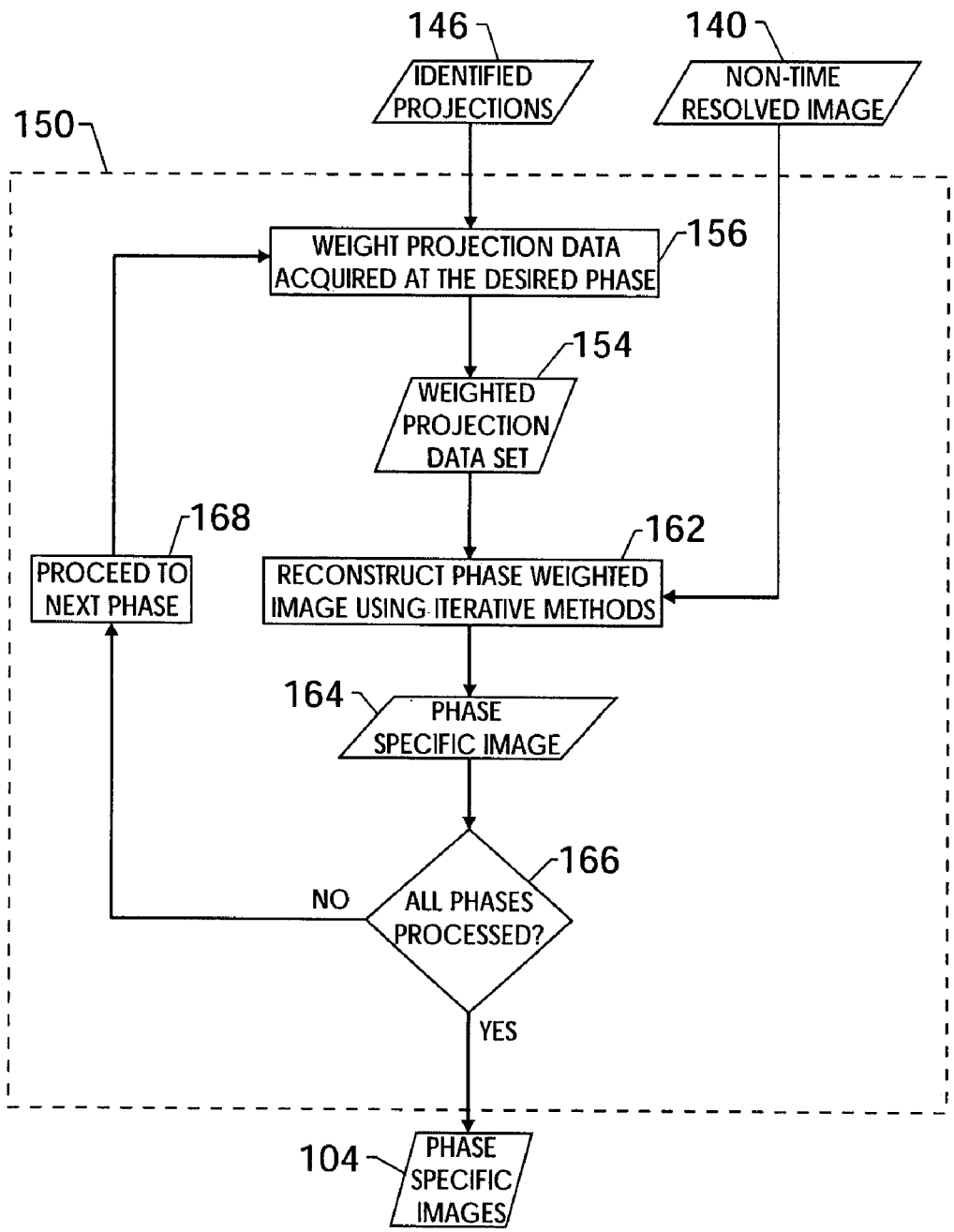
FIG. 6 is a flowchart depicting a technique for reconstructing images for use in determining cardiac motion, in accordance with one aspect of the present technique.

For example, referring to FIG. 5, one technique for generating reconstructions to aid in determining cardiac motion is described in detail. A filtered backprojection of the complete, projection data set 82 acquired during 360° of gantry rotation is performed to reconstruct a non-time resolved image 140, as depicted at step 142. The inconsistencies in the projection data set 82 attributable to cardiac motion result in motion-related artifacts, such as streaking or blurring, in the non-time resolved image 140. The phase data 96 may be used to identify sets of projections in the projection data set 82 which were acquired at the same cardiac phase, as depicted at step 144. The identified projections 146 incorporate the desired phase data with the projections comprising the projection data set 82 and may be used to reconstruct phase-specific images 104, as depicted at step 150 and shown in detail in FIG. 6. In particular, a weighted projection data set 154 is created using the full projection data set 82 by weighting the identified projections 146 associated with the cardiac phase of interest as more important, as depicted at step 156. At the expense of temporal resolution, adjacent views to the views of the phase of interest may be weighted, to an equal or lesser extent, to further reduce image artifacts resulting from statistical noise in the measurements.

Using iterative reconstruction techniques known to those of ordinary skill in the art, the weighted data set 154 may be iteratively reconstructed to update the region of interest, as shown in step 162. The non-time resolved image 140 may be used as a reference or initial image, depending on the iterative methodology employed. The iterative process may continue until the image quality and the temporal definition are determined to be acceptable, at which time it may be considered a phase-specific image 164. The phase-specific image 164 preserves the phase information introduced by the weighting process but also incorporates projections from other phases to contribute to the overall image, thereby improving the overall quality of the image. If desired, only the region of interest corresponding to the heart may be iteratively updated. Feathering may be employed to prevent discontinuities in the phase-specific image 164 between the iteratively updated region of interest and the remainder of the image.

A determination may be made whether phase-specific images 164 exist for all of the phases of interest at decision block 166. If phase-specific images do not exist for all of the phases of interest, the next phase is proceeded to at step 168 and a weighted projection data set 154 is generated for the next phase of interest. Once a phase-specific image 164 exists for all phases of interest, the phase-specific images 104 may be used to identify motion between temporally adjacent images, as depicted at step 170 of FIG. 5. For example, the motion identified between the temporally adjacent, phase-specific images 104 may be used to warp the reconstruction grid at all view angles, as depicted at step 106. The image grid warping for each view angle position corresponds to the phases of the cardiac cycle that the projection data were acquired.

B. Correlation-Based Estimation

One technique for determining motion is an image-based correlation approach. This approach uses the phase data 96 and the projection data 82 to reconstruct phase-specific images 104, as depicted in step 182 of FIG. 7. The phase-specific images 104 may be formed using iterative reconstruction of weighted views, as discussed above with regard to step 162 of FIG. 6. One or more regions of interest in phase-specific images 104 are correlated to respective regions in one or more temporally neighboring phase-specific images 104 to determine the probable motion of the regions of interest over time, as depicted at step 184. An image displacement map 186 may be generated using the probable motion data of the regions of interest generated by the correlation process. In this manner, a displacement map 186 may be generated for each image of the heart over time. The displacement and time information may be combined to form a velocity map for each adjacent pair of phase-specific images 104 if desired. Once velocity and/or displacement maps 186 are generated for each phase of interest, as determined at decision block 188, the motion information may be used to warp the reconstruction grids at the respective view angles, as depicted at step 106. If maps 186 have not been generated for each phase of interest, as determined at decision block 188, the next phase is processed, as depicted at step 190, until all phases of interest have been processed.

Figure 7:
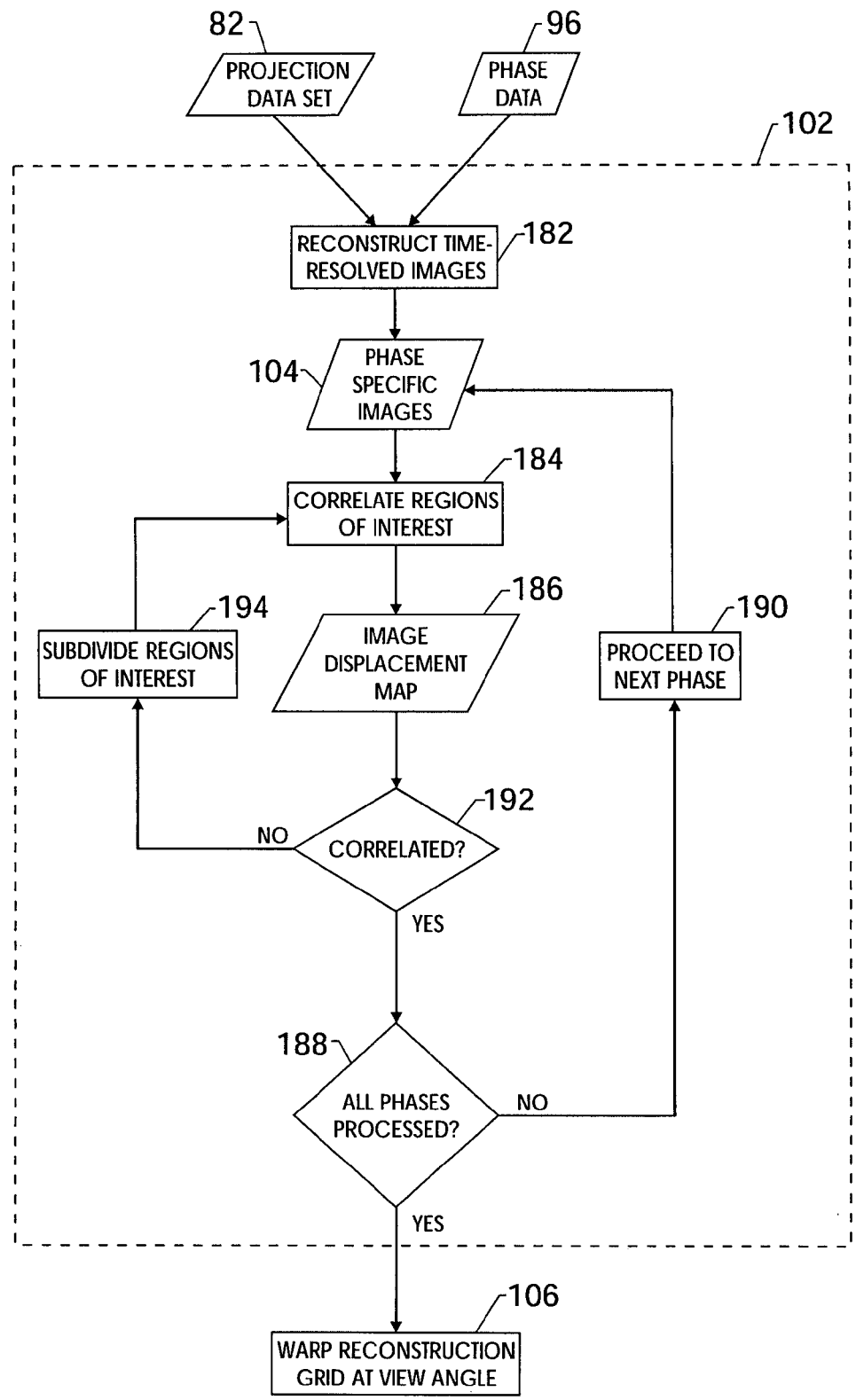
FIG. 7 is a flowchart depicting an additional technique for determining cardiac motion, in accordance with one aspect of the present technique.

As depicted in FIG. 7, a multi-resolution aspect may be incorporated into the correlation-based approach. The multi-resolution aspect may be useful where the regions of interest exhibit complex or multiple directions of motion. In particular, after determination of the motion of the regions of interest, as identified in the velocity and/or displacement map 186, a determination is made at decision block 192 as to whether the temporally adjacent regions of interest are correlated to the desired degree, i.e., if the desired correlation threshold is met or exceeded. For example, a correlation threshold of 95% may be implemented.

If the correlation threshold is met, processing proceeds as described above with any remaining phases being processed and the motion information used to warp the respective reconstruction grids 108. If, however, the correlation threshold is not met or exceeded, the region or regions of interest may be subdivided, as depicted at step 194, and the correlation process repeated until the correlation threshold is met by the subdivided regions of interest. In this manner the complex motion of the heart, or other object, may be determined and accurately used to warp the reconstruction grids at step 106.

C. Wavelet Decomposition

Similarly, wavelet decomposition may be used in the motion determination step 102. This approach uses the phase data 96 and the set of projection data 82 to reconstruct phase-specific images 104 as depicted at step 202 in FIG. 8. The phase-specific images 104 may be formed using iterative reconstruction of weighted views, as discussed above with regard to step 162 of FIG. 6. One or more regions of interest in the phase-specific images 104 are decomposed via a wavelet function, as depicted at step 204, to generate wavelet coefficients 206 for the regions of interest at the phase of interest. In particular, using the relevant wavelet basis functions, the local frequency information of the regions of interest is better captured relative to approaches using Fourier-based analysis performed on the entire image.

The differences between the wavelet coefficients associated with the regions of interest may be analyzed for regions in temporally adjacent reconstructions to generate an image displacement map 208 and/or velocity map describing the local motion of the regions of interest, as depicted at step 210. Once the velocity and/or displacement maps 208 of each phase of interest are generated, as determined at decision block 212, the motion information incorporated in the maps may be used to warp the reconstruction grids at the respective view angles, as depicted at step 106. If maps 208 have not been generated for each phase of interest, the next phase is processed, as depicted at step 214, until all phases of interest have been processed.

As with the correlation-based approach depicted in FIG. 7, a multi-resolution aspect may be incorporated into the wavelet decomposition approach to accommodate complex motion within the regions of interest. In particular, after determination of the motion of the regions of interest from the velocity and/or displacement map 186, a determination may be made at decision block 216 as to whether all of the temporally adjacent regions of interest are correlated to the desired degree, as discussed above with regard to the correlation-based approach.

If the correlation threshold is met, processing proceeds as described above with any remaining phases being processed and the motion information used to warp the respective reconstruction grids. If, however, the correlation threshold is not met or exceeded, the region or regions of interest may be subdivided, as depicted at step 218, and the decomposition and analysis processes repeated until the correlation threshold is met by the subdivided regions of interest. In this manner the complex motion of the heart, or other object, may be determined and accurately used to warp the reconstruction grids at step 106.

D. Sparse, Differential-Projection Image Grid Motion Determination

Figure 9:
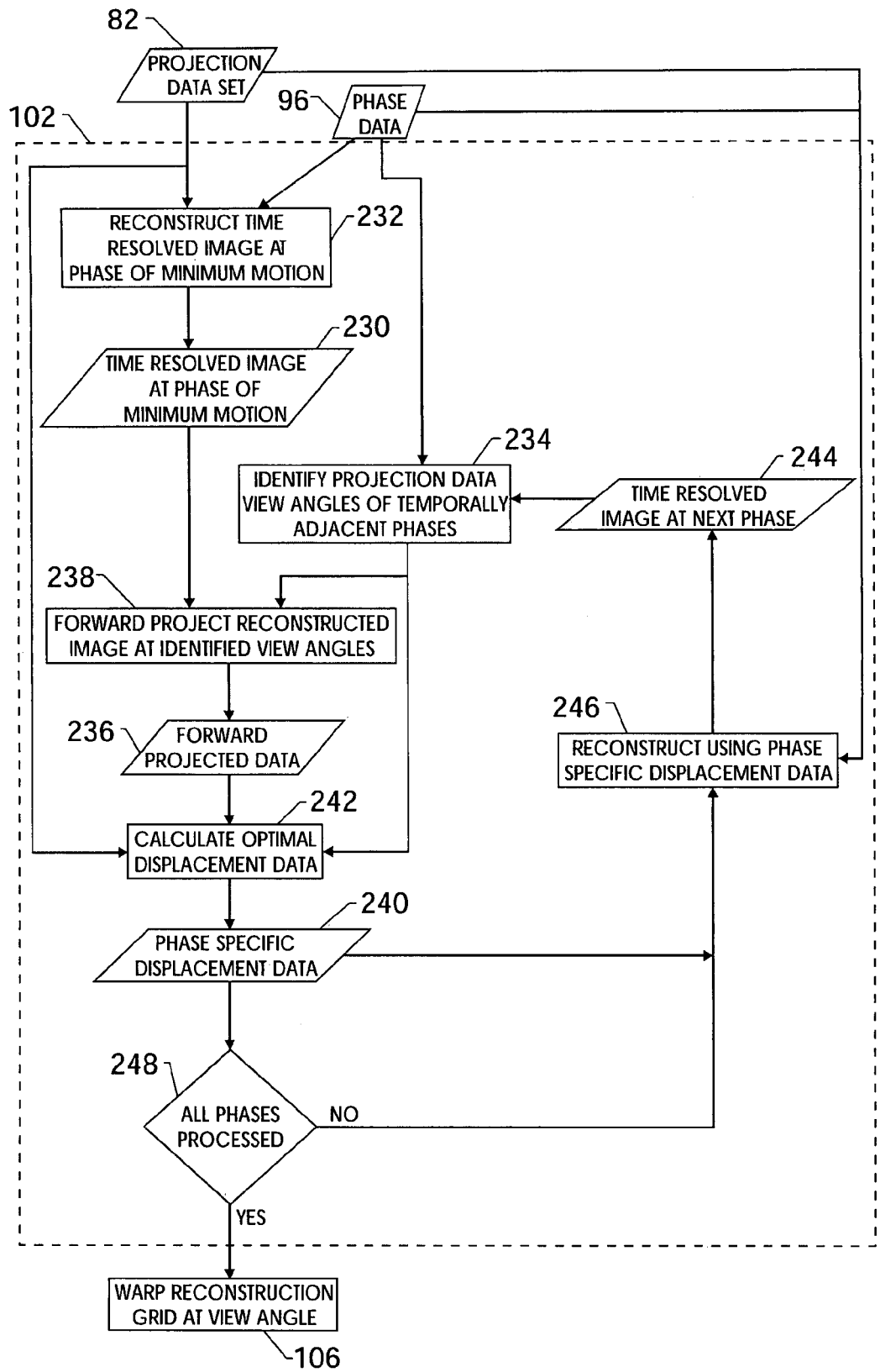
FIG. 9 is a flowchart depicting a further technique for determining cardiac motion, in accordance with one aspect of the present technique.

The motion determination step 102 may also be accomplished by using the projection data 82 and the phase data 96 to reconstruct a time-resolved image at the phase of minimum motion 230, as depicted at step 232 of FIG. 9. Although not discussed, in other embodiments, it is possible to generate the initial images using other techniques. For example, since the non-time resolved image 140 comprises components of the time-resolved images, it may be used with alternate processing steps than described herein to accomplish the same task. Moreover, the initial image can be generated by a variety of reconstruction approaches, for example with filtered back-projection or iterative reconstruction techniques.

The view angles of temporally adjacent phases may be identified using the phase data 96, as depicted at step 234. The time-resolved image 230 may be forward-projected for the identified view angles to generate forward-projected data 236, as depicted at step 238. Phase-specific displacement data 240 may be generated by optimizing, generally by minimizing, the difference between the forward-projected data 236 and the measured projection data 82 at the temporally adjacent phase, as depicted at step 242. For example, minimizing the difference may be accomplished by generating a map of motion estimation that appropriately warps the reconstruction grid during the increment in phase, thereby improving the similarity of the measured data with the forward-projected data. As one might expect, the motion estimates are considered accurate when little or no error exists between the difference of the measured projection data 82 of a temporally adjacent phase, as determined at block 234, and the forward-projected data 236 of the reconstruction volume after applying the phase-specific displacement data 240 to the reconstruction grid.

The optimization and/or minimization process at step 242 may be accomplished by a variety of approaches. For example, the image motion may be linearized and solved iteratively. Alternatively, the problem may be expressed in terms of the optic flow equation, allowing the solution to be determined by the solution of a large set of linear equations. The process may also be accomplished by subtracting the forward-projected data 236 from the measured projection data 82 identified in a temporally adjacent phase at step 234. The differential projection data thereby obtained may be backprojected to generate an image of the temporal derivative of the object motion in the image. The temporal derivative data may then be used to generate a gradient of the original time-resolved image 230 while applying the constraint conditions for optic flow to estimate object motion occurring between reconstructed images of adjacent phases of interest.

The phase-specific displacement data 240 thereby obtained provides a three-dimensional estimate of motion for the time-resolved image 230 and therefore allows the generation of an image 244 at the next temporal phase, as depicted at step 246, by incorporating the image grid warping of the reconstructed images during the backprojection process. The process may be repeated until all phases of interest have been reconstructed, as determined at decision block 248. The phase-specific displacement data 240 thereby generated may be used to warp the reconstruction grids at the respective view angles, as depicted at step 106.

This approach may be modified by parameterizing the motion in the image using a three-dimensional function or set of three-dimensional basis functions. As one skilled in the art will readily understand, the same techniques can be applied to two-dimensional images as well. The coefficients of the functions or functions may be estimated from the displacement data 240 to form the reconstructed image of the next phase 244, as depicted in block 246. This approach provides a way to reconstruct a quantity based upon motion distribution as opposed to the linear attenuation coefficients visualized as intensities. Alternately, both the motion distribution and the linear attenuation can be reconstructed simultaneously in a similar fashion.

E. Time-Resolved, Differential-Projection Modeled Motion Determination

Figure 10:
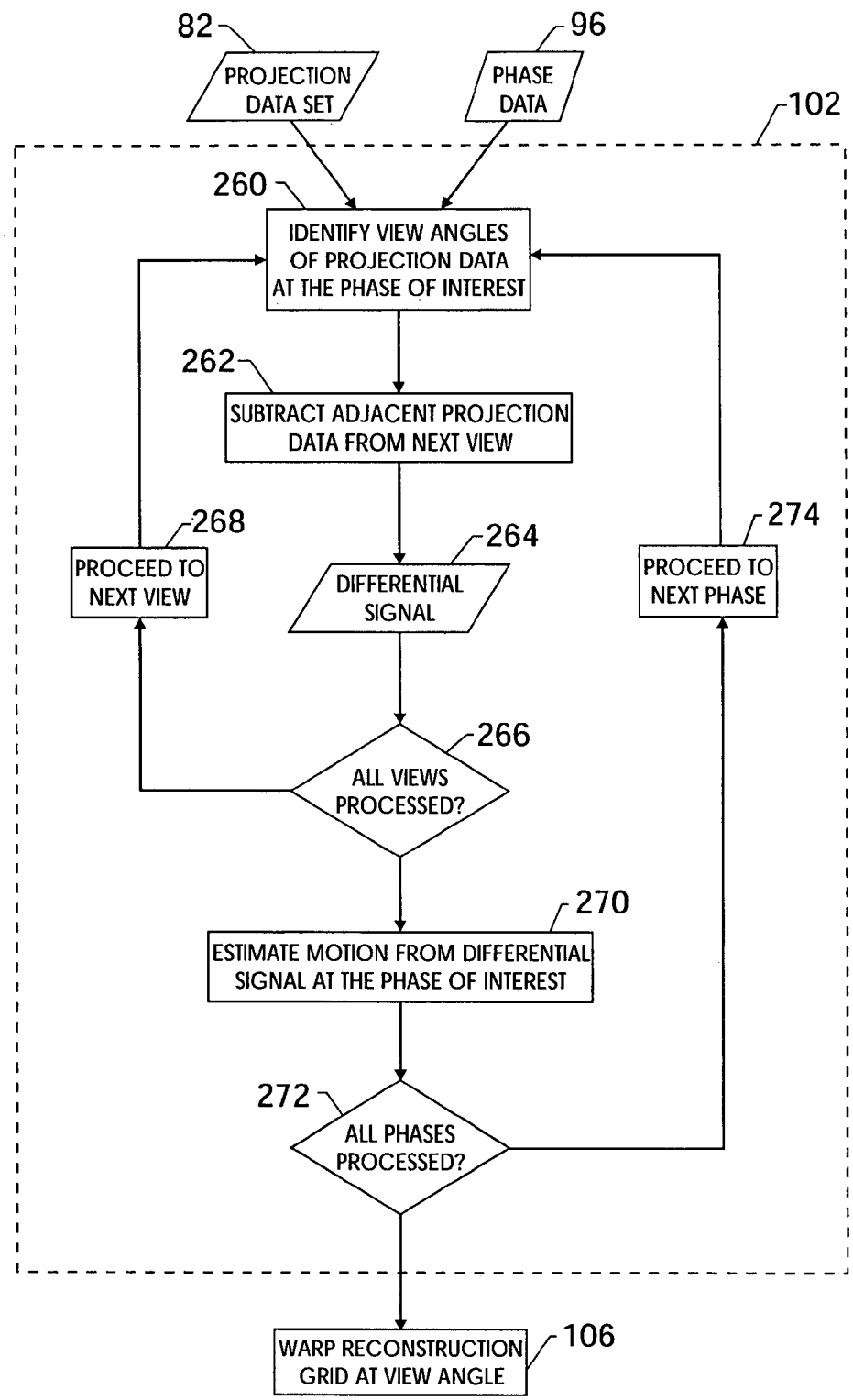
FIG. 10 is a flowchart depicting an additional technique for determining cardiac motion, in accordance with one aspect of the present technique.

The motion determination step 102 may also be accomplished by using the projection data 82 and the phase data 96 to identify the view angles of projection data at the phase of interest, as depicted at step 260 of FIG. 10. The projection data set from the next adjacent view is subtracted from the projection data at the phase of interest at step 262 to generate a differential signal 264. The differential signal 264 represents the motion of the object between the two views along a substantially common ray. The motion of the heart may be estimated from the differential signal 264 in accordance with the null space, i.e., the motion of the heart can be estimated orthogonal to, but not along the ray comprising the differential signal 264. If desired a correction factor may be introduced to account for the rotation of the object, i.e., the heart, as represented in the differential signal 264.

If additional views of the phase of interest remain, as determined at decision block 266, the process proceeds to the next view, as depicted at step 268, until all views of the phase of interest have been processed. The motion of the heart within the image may be determined from the combined differential signals, as depicted at step 270. The respective reconstruction grids may be warped at the respective view angles, as depicted at step 106, using the motion data determined from the combined differential signals 264. If additional phases of interest remain to be processed, as determined at step 272, the process proceeds to the next phase, as depicted at step 274, and continues until motion estimation is generated for each view of each phases of interest.

As one of ordinary skill in the art will appreciate, the processes for determining and correcting motion described herein may be provided as one or more routines executable by the computer 36 or by other processor-based components of the CT system 10. The routines may be stored or accessed on one or more computer-readable media, such as magnetic or optical media, which may be local to the computer 36 or processor-based component or may be remotely accessible via a network connection, such as via the Internet or a local area network Furthermore, access to or operation of the routines may be provided to an operator via the operator workstation 40 as part of the normal operation of a CT imaging system 10.

While the above techniques are useful in the determination of cardiac motion for use in reconstructing motion-corrected images and for improving the temporal resolution of reconstructed images, other techniques may also be employed and are within the scope of this disclosure. Likewise, the present techniques for reconstructing motion-corrected images and for determining motion may be applied to the imaging of moving objects other than the heart. Indeed, discussion of cardiac imaging is presented merely to facilitate explanation of the present techniques. Additionally, use of the motion estimates in the invention has been discussed in the context of filtered back-projection reconstruction techniques. However, the motion estimates may be used with other reconstruction strategies, such as with iterative reconstruction techniques.

Indeed, while the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for CT imaging, comprising the acts of:
   acquiring radiographs during one or more rotations or a partial rotation of a gantry about a dynamic object, wherein the gantry takes at least five seconds to complete a half rotation;
   generating a projection data set from the radiographs;
   deriving motion data for the dynamic object based upon the projection data set and/or upon images generated using the projection data set; and
   improving the temporal resolution of a reconstruction process applied to the projection data set by utilizing the motion data.

2. The method as recited in claim 1, wherein the dynamic object is a heart.

3. The method as recited in claim 1, wherein the reconstruction process comprises backprojecting the projections corresponding to a view angle onto a warped reconstruction grid.

4. The method as recited in claim 1, wherein the projection data set is acquired during one rotation of the CT gantry which takes ten or more seconds to complete.

5. The method as recited in claim 1, wherein the reconstruction process comprises an iterative reconstruction process.

6. The method as recited in claim 1, wherein the reconstruction process comprises a phase-specific reconstruction process.

7. A computer program, provided on one or more computer readable media, for CT imaging, comprising:
   a routine configured to acquire radiographs during one or more rotations or a partial rotation of a gantry about a dynamic object, wherein the gantry takes at least five seconds to complete a half rotation;
   a routine configured to generate a projection data set from the radiographs;
   a routine configured to derive motion data for the dynamic object based upon the projection data set and/or upon images generated using the projection data set; and
   a routine configured to improve the temporal resolution of a reconstruction process applied to the projection data set by utilizing the motion data.

8. The computer program as recited in claim 7, wherein the dynamic object is a heart.

9. The computer program as recited in claim 7, wherein the reconstruction process comprises backprojecting the projections corresponding to a view angle onto a warped reconstruction grid.

10. The computer program as recited in claim 7, wherein the reconstruction process comprises an iterative reconstruction process.

11. The computer program as recited in claim 7, wherein the reconstruction process comprises a phase specific reconstruction process.

12. A CT image analysis system, comprising:
    a gantry comprising an X-ray source configured to emit a stream of radiation, wherein the gantry takes at least five seconds to complete a half rotation;
    a detector configured to detect the stream of radiation and to generate one or more signals responsive to the stream of radiation, wherein the detector comprises a plurality of detector elements;
    a system controller configured to control the X-ray source and to acquire radiographs via the detector as the X-ray source is rotated about a dynamic object; and
    a computer system configured to generate a set of projection data from the radiographs, to derive motion data for the dynamic object based upon the projection data set and/or upon images generated using the projection data set, and to improve the temporal resolution of a reconstruction process applied to the projection data set by utilizing the motion data.

13. The CT image analysis system, as recited in claim 12, wherein the dynamic object is a heart.

14. The CT image analysis system, as recited in claim 12, wherein the reconstruction process comprises backprojecting the projections corresponding to a view angle onto a warped reconstruction grid.

15. The CT image analysis system, as recited in claim 12, wherein the reconstruction process comprises an iterative reconstruction process.

16. The CT image analysis system, as recited in claim 12, wherein the reconstruction process comprises a phase specific reconstruction process.

* * * * *

UNITED STATES PATENT AND TRADEMARK OFFICE
CERTIFICATE OF CORRECTION

PATENT NO. : 7,382,852 B2
APPLICATION NO. : 11/804861
DATED : June 3, 2008
INVENTOR(S) : Edic et al.

It is certified that error appears in the above-identified patent and that said Letters Patent is hereby corrected as shown below:

On the Title Pg, Item 56, under "U.S. PATENT DOCUMENTS", Line 1, delete "11/1944" and insert -- 2/1944 --, therefor.

On the Title Pg, on Page 2, Item 56, under "U.S. PATENT DOCUMENTS", below Line 6, insert -- 5,396,408    03/1995 Szczech, III --, therefor.

On the Title Pg, on Page 2, Item 56, under "U.S. PATENT DOCUMENTS", Line 26, delete "2004/0014710" and insert -- 2004/0114710 --, therefor.

Figure 8:
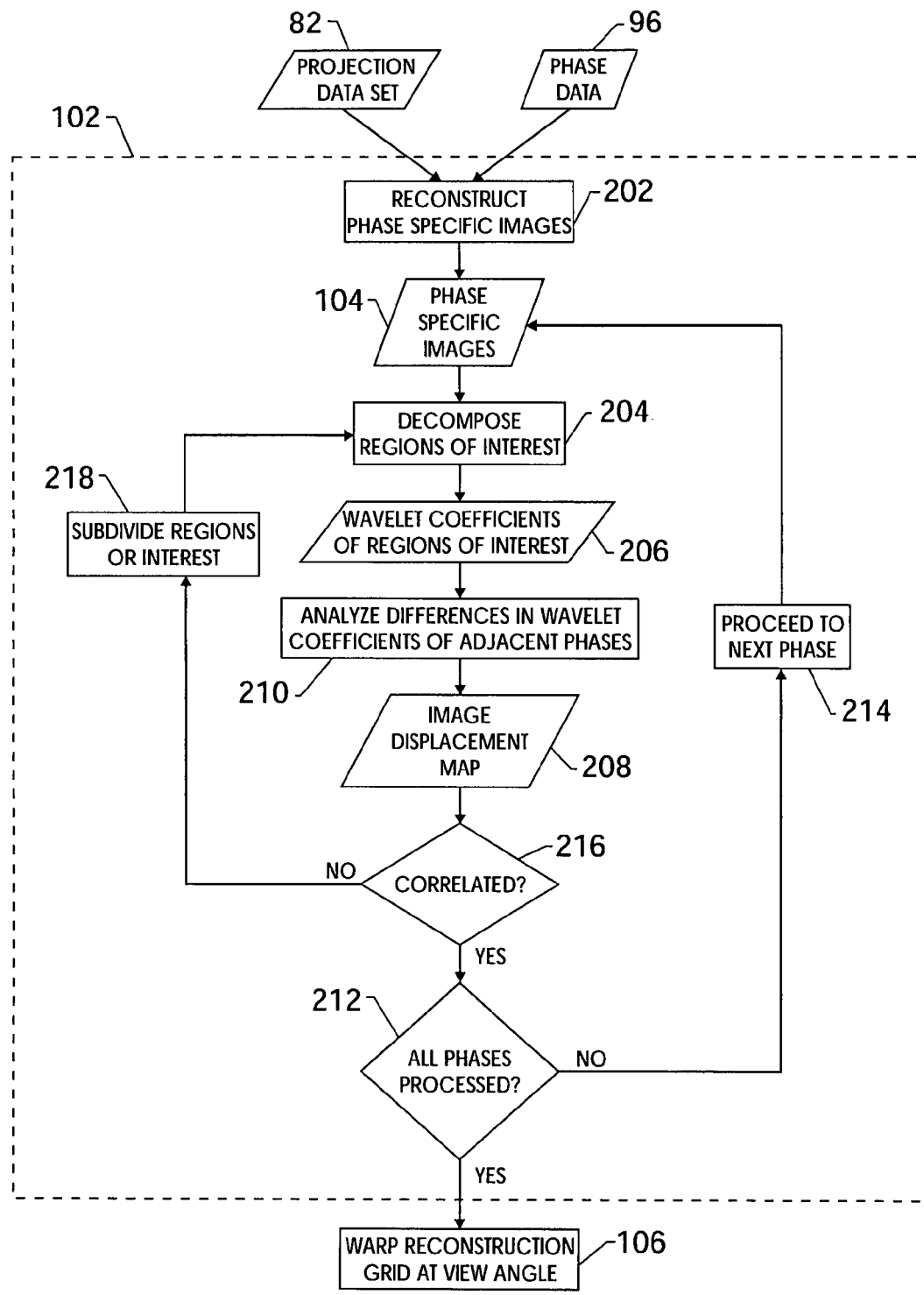
FIG. 8 is a flowchart depicting another technique for determining cardiac motion, in accordance with one aspect of the present technique.

In Fig. 8, Sheet 8 of 10, for Tag "218", Line 2, delete "OR" and insert -- OF --, therefor.

In Column 13, Line 19, delete "network" and insert -- network. --, therefor.

Signed and Sealed this

Twenty-eighth Day of July, 2009

JOHN DOLL
*Acting Director of the United States Patent and Trademark Office*